US006982789B1

(12) United States Patent  (10) Patent No.: US 6,982,789 B1
Meyer  (45) Date of Patent: Jan. 3, 2006

(54) MONOCHROMATOR SYSTEM AND APPLICATIONS THEREOF

(75) Inventor: Duane E. Meyer, Lincoln, NE (US)

(73) Assignee: J.A. Woollam Co. Inc., Lincoln, NE (US)

( * ) Notice: Subject to any disclaimer, the term of this patent is extended or adjusted under 35 U.S.C. 154(b) by 318 days.

(21) Appl. No.: 10/637,051

(22) Filed: Aug. 8, 2003

Related U.S. Application Data

(63) Continuation-in-part of application No. 09/531,877, filed on Mar. 21, 2000, now Pat. No. 6,535,286.

(60) Provisional application No. 60/431,489, filed on Dec. 6, 2002.

(51) Int. Cl.
 *G01J 3/12* (2006.01)
(52) U.S. Cl. .................... 356/331; 356/328; 356/367; 356/369
(58) Field of Classification Search ........ 356/364–369, 356/300, 310, 318–322, 326–331, 333, 334; 250/225, 237 R, 237 G
See application file for complete search history.

(56) References Cited

U.S. PATENT DOCUMENTS

| | | |
|---|---|---|
| 1,773,436 A | 8/1930 | Rayton |
| 2,926,537 A | 3/1960 | Piejerse |
| 3,405,270 A | 10/1968 | Briggs |
| 3,630,621 A | 12/1971 | Lishowitz |
| 4,062,251 A | 12/1977 | Parsons ........................ 74/501 |
| 4,242,581 A | 12/1980 | Crow ......................... 250/227 |
| 4,656,780 A | 4/1987 | Miyauchi et al. ............. 49/348 |
| 4,938,602 A | 7/1990 | May et al. ................... 356/435 |
| 5,166,752 A | 11/1992 | Spanier et al. .............. 356/369 |
| 5,303,035 A | 4/1994 | Luecke et al. ............... 356/399 |
| 5,494,829 A | 2/1996 | Sandstrom et al. ......... 436/518 |
| 5,661,589 A | 8/1997 | Meyer ........................ 359/232 |
| 5,757,494 A * | 5/1998 | Green et al. ................. 356/369 |
| 5,872,630 A * | 2/1999 | Johs et al. ................... 356/369 |
| 5,956,145 A * | 9/1999 | Green et al. ................. 356/364 |
| 6,042,298 A | 3/2000 | Mastrogiannis et al. .... 403/402 |
| 6,084,675 A | 7/2000 | Herzinger et al. .......... 356/369 |
| 6,278,519 B1 | 8/2001 | Rosencwaig et al. ....... 356/369 |
| 6,353,477 B1 | 3/2002 | Johs et al. ................... 356/369 |
| 6,414,302 B1 | 7/2002 | Freeouf ...................... 250/225 |

* cited by examiner

*Primary Examiner*—Gregory J. Toatley, Jr.
*Assistant Examiner*—Roy M. Punnoose
(74) *Attorney, Agent, or Firm*—James D. Welch

(57) ABSTRACT

A monochromator system applicable in spectrophotometer, polarimeter and ellipsometer systems which operate over a large range of wavelengths, including a stage which enables position adjustment of the location of a source of electromagnetic radiation in lateral (X), longitudinal (Y) and vertical (Z) directions, from a common location outside an enclosure, and including multiple detector systems mounted in a manner which allows easily, sequentially, via mechanical motion, placing a first and then a second thereof so as to receive a beam of electromagnetic radiation.

7 Claims, 11 Drawing Sheets

MONOCHROMATOR SYSTEM AND APPLICATIONS THEREOF

This Application is a CIP of Allowed application Ser. No. 09/531,877, filed Mar. 21, 2000, (now U.S. Pat. No. 6,535, 286), via Co-Pending application Ser. No. 10/376,677, Filed Feb. 28, 2003, and claims Benefit of Provisional Application 60/431,489 Filed Dec. 6, 2002.

TECHNICAL FIELD

The disclosed invention relates to monochromator systems for use in selecting specific wavelengths in a plurality thereof, and more specifically to a monochromator system suitable for use in polarimeter, ellipsometer and spectrophotometer and the like systems, which monochromator system is mounted in a substantially enclosed space within an enclosing means, said monochromator system being distinguished in that electrical connections to internally mounted slit, grating, source selecting mirror controlling stepper motors, and order selecting filters are to a mother printed circuit board via plug-socket means. The mother printed circuit board further interconnects, via plug/socket means to stepper motor control electronic components mounted externally to said enclosing means. In addition, a source of an electromagnetic radiation beam inside said enclosing means is mounted to a stage which enables position adjustment thereof in lateral (X), longitudinal (Y) and vertical (Z) directions from a common location outside said enclosing means without the requirement that the substantially enclosed space be opened to atmosphere.

BACKGROUND

To begin it is disclosed that the bi-lateral slit assembly of Co-owned U.S. Pat. No. 5,661,589 is revisited as part of the presently disclosed invention. Further, the disclosed invention includes in some embodiments a multiple detector system as disclosed in Allowed application Ser. No. 09/531, 877, (now U.S. Pat. No. 6,535,286), from which this Application Continues-in-Part via Co-Pending application Ser. No. 10/376,677, Filed Feb. 28, 2003.

Spectroscopic ellipsometry (SE) was developed in the early 1970's after single wavelength ellipsometry had gained widespread acceptance. The first (SE) systems provided limited Ultraviolet (UV) to near Infrared (IR) spectral range capability, and with the exception of a few research instruments, this remained the case until the 1990's. Many challenges faced development of (VUV) ellipsometer systems, including the fact that many optical element materials absorb in the (VUV) wavelength range. Vacuum Ultraviolet (VUV) ellipsometry was so named as it was initially carried out in vacuum, however, the terminology is today applied where purging gas such as nitrogen or argon is utilized in place of vacuum at wavelengths, typically with an energy less than about 10 ev. The reason (VUV) ellipsometry must be carried out in vacuum or purging gas is that (VUV) wavelengths, are absorbed by oxygen and water vapor.

In the mid-1980's a Spectroscopic ellipsometer was constructed at the BESSY Synchrotron in Berlin for application in the (VUV) wavelength range, (eg. 5–35 eV), and in the 1990's Spectroscopic ellipsometry was achieved in the Extreme Ultraviolet (EUV) range, (eg. greater than 35 eV), at KEK-PF. Application of ellipsometry in the (VUV) and (EUV) wavelength ranges remained restricted to said research facilities until in 1999 commercial (VUV) ellipsometer systems became available from companies such as the J.A. Woollam Co. Inc. At present there are approximately twenty-five (VUV) Systems in use worldwide. It is noted that commercial (VUV) instruments, which provided wavelengths down to 146 nm, were introduced in response to the need for bulk material properties at 156 nm, which is utilized in lithography as applied to semiconductor gate oxide production.

The practice of ellipsometry, polarimetry, spectrophotometry, reflectometry, scatterometry and the like, using Infrared (IR), (eg. 2–33 micron), and Ultraviolet (UV), (eg. 135–1700 nm), Electromagnetic Radiation Wavelengths, then is, as disclosed above, known. As mentioned, electromagnetic Radiation with wavelengths below about 190 nm is absorbed by atmospheric components such as Oxygen and Water Vapor. Thus, practice of Ellipsometry etc. using VUV Wavelengths is typically carried out in vacuum or an atmosphere which does not contain oxygen and/or water vapor or other absorbing components. The J.A. Woollam CO. VUV-VASE, (Registered Trademark), for instance, utilizes a Chamber which encompasses a substantially enclosed space which during use is purged by Nitrogen and/or Argon or functionally equivalent gas. (Note Nitrogen does not significantly absorb UV Range wavelengths above about 130 nm, and Argon is in some respects even a better choice as it has an even lower yet onset of UV Range wavelength absorption). Further, the source of the electromagnetic radiation in the J.A. Woollam CO. VUV-VASE is preferably a Deuterium Lamp or a Xenon Lamp present within a J.A. Woollam Co. monochromator system which produces wavelengths of 115–400 nm, (of which 135–190 nm is used), and up to about 2000 nm, respectively. Specific wavelengths are selected by said J.A. Woollam Co. Monochromator which comprises a specially designed Cherny-Turner Spectrometer.

It is beneficial to note that Spectroscopic Ellipsometry (SE) is practiced utilizing an ellipsometer system generally comprising:
   a source system comprising:
      a source of electromagnetic radiation: and
      a polarization state modifier system:
   a stage for supporting a sample system;
   a plurality of polarization state detector systems, each of which comprises:
      a polarization state analyzer: and
      a detector system;

such that a beam of electromagnetic radiation is produced by said source of electromagnetic radiation and caused to pass through said polarization state modifier system, interact with a sample system placed on said stage for supporting a sample system, pass through a polarization state analyzer and enter a detector system in the pathway thereof. It is noted that the terminology "a source" can include multiple sources which serve to provide a beam of electromagnetic radiation in different wavelength ranges.

The standard J.A. Woollam CO. VUV-VASE Spectroscopic Ellipsometer system sequentially comprises, mounted inside substantially enclosed space within a Chamber:
   a monochromator;
   a beam polarizing means;
   a polarization state modifying means as described in U.S. Pat. Nos. 5,956,145 and 5,757,494;
   a beam alignment detector means such as a quad detector as mentioned in U.S. Pat. No. 5,872,630 in Col. 20, Lines 55–57;
   a stage for supporting a sample system;

an analyzing means; and
data detector means;

wherein said monochromator comprises;
   a) source of electromagnetic radiation;
   b) a first slit in a first slit providing means;
   c) a first mirror;
   d) a first stage comprising a plurality of gratings, each of which can be rotated into a functional position;
   e) a second mirror;
   f) a second slit in said second slit providing means;
   g) a third mirror
   h) a second stage comprising a plurality of gratings, each of which can be rotated into a functional position;
   i) a fourth mirror;
   j) order sorting filter means;
   k) a pin hole;

with a beam chopper being present after said source of electromagnetic radiation, (typically, but not necessarily, just prior to said pin hole).

In use an electromagnetic beam from said source of the electromagnetic radiation is:
   caused to pass through said first slit;
   reflect from said first mirror;
   interact with one of said plurality of gratings on said first stage which is rotated into a functional position;
   reflect from said second mirror;
   pass through said second slit;
   reflect from said third mirror;
   interact with one of said plurality of gratings on said second stage which is rotated into a functional position;
   reflect from said fourth mirror; and
   proceed through order sorting filtering means; with monochromator selected wavelengths being caused to exit through said pinhole.

The beam is also chopped by beam chopping means placed somewhere after the source of electromagnetic radiation, (typically, but not necessarily, just before the pin hole providing means).

The gratings on said first and second stages are independently rotated into precise desired functional positions via stepper motors controlled by computer. This has proven to provide superior precision and repeatability than commercially available grating positioning systems, at least in part because the J.A. Wobllam Co. system does not control one grating supporting stage as a slave to the other, as is done in known competing systems. Again, in use, the stages which support the gratings are independently rotated to optimum orientations.

Further, it is disclosed that an electromagnetic radiation beam produced by said J.A. Woollam CO. Monochromator has been shown to provide a highly collimated beam, with typical defining parameters being a 5 mm diameter at the pinhole output of the Monochromator, with divergence to about 20 mm diameter at 20 Feet, (ie. 6000 mm). This represents a divergence angle of only about 0.00125 radians, (ie. 0.07 Degrees). The collimating optics comprises a spherical mirror in the optical path after the pinhole. Said spherical mirror collimates the beam and directs it to a flat folding mirror, and said flat folding miror directs the beam out of the monochromator.

While not new, it is noted that alignment of the Xenon Lamp follows a two step procedure. First it must be understood that the Xenon Lamps used have an Ellipsoidal Reflector associated therewith, which has a focal length and major and minor axes. The first step is to place the Xenon Lamp into the focal length position. This is followed by adjusting the major axis of the Ellipsoidal Reflector to be in line with the First Slit. The alignment procedure is typically monitored by maximizing intensity output from the Pin Hole.

It is also noted that the Deuterium and/or Xenon sources of electromagnetic radiation can be placed as indicated, but separate from the other components of the monochromator. For instance, in an ellipsometer system which sequentially comprises the Deuterium and/or Xenon sources in a Polarization State Generation System (PSG), a Sample System supporting Stage and a Polarization State Detector System (PSD), the components other than the Source of Electromagnetic Radiation can be placed in any functional location before or after the Sample System between the (PSG) and (PSD) or within one and/or the other.

Continuing, problems have been identified with application of the J.A. Woollam Co. monochromator system sold to date in that electrical wiring and motor driver electronic components have been included inside the substantially enclosed space in which specific wavelengths in electromagnetic beams are selected. As mentioned, outgassing from anything inside said substantially enclosed space can require very long periods of time, and substantial purging can be required where Vacuum-Ultraviolet (VUV) wavelengths are utilized. Further, diminished throughput of electromagnetic radiation with time has been traced to be, at least in part, caused by deposition and polymerization of polymers present in wire coatings on optical surfaces such as the surfaces of the mirrors and gratings inside the substantially enclosed space. It is also identified that electrical connections to components, such as the means for providing the first and second slits and rotation effecting means for the first and second grating stages, and the Lamp selecting mirror have, to date, been hard wired inside the enclosing means, thereby making replacement tedious. Further, the position of electromagnetic radiation source means present inside said substantially enclosed space must be adjusted to provide a beam which follows an intended locus. To date, position adjustments have required opening the enclosing means, thereby requiring additional purging where UV wavelengths are utilized.

Known patents include U.S. Pat. No. 5,303,035 to Ludcke et al., which describes a precision micropositioner that allows up to six degrees of motion freedom which are adjustable from controls located in a single plane. The mechanism involves forcing balls between support and ramped elements. It is noted that the range of adjustment is limited by the slope and length of the ramped elements. Specifically the present invention enables a greater range of adjustment. Other patents which describe the use of balls to transmit motion include No. 6,042,298 to Mastrogiannis et al. which describes the use of two sequences of balls oriented in manner so that forcing a wedge shape between the first ball in each sequence causes coupling of a joint between two sections in a frame. U.S. Pat. No. 4,656,780 to Miyauchi et al. describes an apparatus for reciprocally moving an object involving a string of interconnected balls. U.S. Pat. No. 4,062,251 to Parsons describes a sequence of interconnected balls in a ball cage, for the purpose of transmiting motion. U.S. Pat. No. 3,204,480 to Bradbury describes a motion transmitting means, again using a sequence of interconnected balls. U.S. Pat. No. 1,807,914 to Hopkins describes a lifting jack which incorporates use of a sequence of balls to transmit motion.

U.S. Pat. No. 6,414,302 B1 to Freeouf is identified as it describes use of VUV wavelengths which range up through 10 eV in systems which are used to investigate properties of solids.

Known patents pertaining to Multiple Detector Systems include a patent to Briggs, U.S. Pat. No. 3,405,270 describing a system containing slots which allow positioning of a source and detector relative to one another. A patent to Rayton et al., U.S. Pat. No. 1,773,436 describes a polarization photometer system with a bracket arm rotatable secured to a post, which is used to support a table and test specimen. U.S. Pat. No. 4,242,581 to Crow, describes a system of four laser energy detectors arranged to allow simultaneous energy monitoring, which system can be easily positioned with respect to a laser beam source aperture. U.S. Pat. No. 3,630,621 to Liskowitz provides a system for measurement of visibility through a fluid using polarized light wherein a source and a detector which are easily positioned with respect to one another. Other patents identified, but not felt to be particularly relevant are U.S. Pat. No. 4,938,602 to May et al., and U.S. Pat. No. 5,494,829 to Sandstrom et al. Patents identified by the Examiner in prosecution of the patent application Ser. No. 09/531,877, filed Mar. 21, 2000 include patent to Green et al. U.S. Pat. No. 5,956,145, patent to Johs et al. U.S. Pat. No. 6,353,477, patent to Rosencwaid et al. U.S. Pat. No. 6,278,519, patent to Herzinger et al. U.S. Pat. No. 6,084,675, previously identified patent to Johs et al. U.S. Pat. No. 5,872,630, patent to Drevillion et al., U.S. Pat. No. 5,557,671 and patent to Spanier et al., U.S. Pat. No. 5,166,752.

The disclosed invention provides improvements to the existing J.A. Woollam Co. monochromator system which are aimed at overcoming the identified problems.

DISCLOSURE OF THE INVENTION

The invention herein is a monochromator system for selecting a small range of wavelengths in a source beam of polychromatic electromagnetic radiation, a substantially enclosed space containing enclosing means thereof having longitudinal and lateral and vertical dimensions. Said disclosed monochromator system functionally sequentially comprises, within said substantially enclosed space containing enclosing means:

a) means for providing of a beam of electromagnetic radiation;
b) a first slit in a first slit providing means;
c) a first mirror;
d) a first stage comprising a plurality of gratings, each of which can be rotated into a functional position;
e) a second mirror;
f) a second slit in said second slit providing means;
g) a third mirror;
h) a second stage comprising a plurality of gratings, each of which can be rotated into a functional position;
i) a fourth mirror;
j) order sorting filter means;
k) a pin hole;

and beam chopper means positioned after the means for providing of a beam of electromagnetic radiation, (typically, though not necessarily, just prior to said pin hole providing means).

Said means for providing of a beam of electromagnetic radiation is, in the preferred embodiment, comprised of two Sources of Electromagnetic Radiation, namely a Deuterium Lamp and a Xenon Lamp, which produce wavelengths of 115–400 nm, (of which 135–190 nm is used), and wavelengths up to about 2000 nm, respectively. A single Lamp Source or more than two Lamp Sources can also be utilized. It is noted that the large range of wavelengths often requires use of multiple Detectors as described in U.S. Pat. No. 6,535,286 from which this Application is a CIP.

Continuing, the Xenon Lamp and its associated power supply are both mounted to the substantially enclosed space defining enclosing means at one longitudinal end thereof to provide a beam of electromagnetic radiation directly to said first slit providing means, with the Xenon Lamp per se. The Deuterium Lamp is mounted inside said substantially enclosed space defining enclosing means per se., with its power supply being mounted laterally adjacent to the Xenon Lamp and its associated power supply at the same longitudinal end of said substantially enclosed space defining enclosing means. It is noted that the power supply for the Xenon and Deuterium Lamps could be located elsewhere, and are located as described only for convenience. Teflon, (Registered Trademark), coated wiring present within the substantially enclosed space provides electrical connection between the Deuterium Power supply and the Deuterium lamp. In use a Source Beam Directing Mirror is positioned to allow the Xenon Beam to pass, or to block said Xenon Beam pathway and direct a Beam from said Deuterium Lamp along essentially the same pathway as the Xenon Beam otherwise travels. Said Source Beam Directing Mirror has associated therewith a motion imparting stepper motor which is provided control power and signal via said Mother Printed Circuit Board. It is noted that presently the Xe Source comprises an Elliptical Mirror and the Deuterium Source comprises a Spherical Mirror for focusing and Steering a beam of electromagentic radiation.

The first and second slit providing means each comprise a narrow opening which is effected by a bilateral slit assembly as claimed in U.S. Pat. No. 5,661,589 which comprises two slide assemblies, each slide assembly comprising an elongated rail element and a slide element such that said slide element can slide with respect to said elongated rail element in the direction of elongation thereof, wherein said two slide assemblies are oriented, by affixing said elongated rail elements to a frame, such that slide element's loci of motion converge toward a lower extent of said frame, as said bilateral slit assembly is viewed in vertically oriented frontal elevation, thereby forming an upward opening "V" shape therebetween, the lower ends of each slide element comprising means for allowing horizontal motion therebetween when said slide element lower ends are caused to simultaneously move vertically during use, which bilateral slit assembly further comprises two knife-blade elements, one affixed to each slide element such that a horizontal slit width between vertically oriented facing edges of said two knife-blade elements can be controlled between essentially zero (0) distance and some larger distance by a simultaneous vertically oriented motion of the lower ends of said slide elements during use. The purpose of controlling said horizontal slit width between vertically oriented facing edges of said two knife-blade elements being to control the intensity and frequency bandwidth of a light beam which can pass therebetween, as is required by spectrometers, monochromators, and spectrographs and the like. Said means for causing the simultaneous motion of said slide elements during use is preferably a precisely controlled computer driven stepper motor which causes a threaded motor shaft therein to move vertically as a result of screw thread translation of motor imparted rotational motion to said threaded motor shaft, said vertical motion causing said slide elements to simultaneously move vertically during use, said precisely controlled computer driven stepper motor being firmly affixed to said frame so that the relative positioning between it and the slide assemblies is rigidly fixed during use.

An alternative and new design, presently in the development stage, for first and second slit providing means again comprises two knife-blade elements affixed to slide elements such that a horizontal slit width between vertically oriented facing edges of said two knife-blade elements can be controlled between essentially zero (0) distance and some larger distance by horizontal oriented motion of one or the other or both thereof during use. Motion translation is via motion of a wedge which contacts two sequences of balls, the first in each sequence of balls contacting the wedge and the last ball in one sequence contacting one of the two knife blades, and the last ball in the other sequence contacting the other of the two knife blades. Causing the wedge to move causes the first ball in each sequence of balls to move and in turn the last ball in each sequence effects motion of the knife blade it contacts. It is specifically noted that the two sequences of balls contact opposite sides of the wedge.

Said first and second stages which each comprise a plurality of gratings, each has associated therewith a rotation imparting means which when provided an electrical signal causes rotation of said associate first or second stage. Further, the preferred embodiment provides three gratings on each of said first and second stages, said gratings-presenting with:

140 nm Blaze Angle and 1200 Grooves per mm;
400 nm Blaze Angle and 1200 Grooves per mm;
1200 nm Blaze Angle and 600 Grooves per mm.

(Note that other function providing Gratings with different grating number per milimeter and/or blaze angles and/or groove spacings could also be applied).

Said second mirror is laterally present between said first mirror and said second stage which comprises a plurality of gratings, and said third mirror being laterally positioned between said first stage which comprises a plurality of gratings and said fourth mirror.

Said first mirror and second mirror and said second stage comprising a plurality of gratings as a group being longitudinally removed from said first stage which comprises a plurality of gratings and said third mirror and said fourth mirror.

First electromagnetic radiation blocking baffle means is positioned between said source means for providing of a beam of electromagnetic radiation and said first stage comprising a plurality of gratings.

Second electromagnetic radiation blocking baffle means is positioned between said second mirror providing-element and said second stage comprising a plurality of gratings.

Third electromagnetic radiation blocking baffle means is positioned between said third mirror providing element and said first stage comprising a plurality of gratings.

Fourth electromagnetic radiation blocking baffle means is positioned between said first and second mirrors.

Fifth electromagnetic radiation blocking baffle means is positioned between said third and fourth mirrors.

Sixth electromagnetic radiation blocking baffle means is positioned between said second stage comprising a plurality of gratings and said pin hole providing means.

The baffle means generally serve to prevent stray electromagnetic radiation from entering the path of the intended electromagnetic beam.

In use a beam of electromagnetic radiation provided by said means for providing of a beam of electromagnetic radiation is:
  caused to pass through said first slit;
  reflect from said first mirror;
  interact with one of said plurality of gratings on said first stage which is rotated into a functional position;
  reflect from said second mirror;
  pass through said second slit;
  reflect from said third mirror;
  interact with one of said plurality of gratings on said second stage which is rotated into a functional position;
  reflect from said fourth mirror, proceed through order sorting filtering means;

said beam being chopped by beam chopping means after said source means for providing of a beam of electromagnetic radiation, (typically, but not necessarily just prior to said pin hole providing means);
  with monochromator selected wavelengths being caused to exit through said pinhole.
  Improvements are that:
  a mother printed circuit board which is present in said substantially enclosed space defining enclosing means, above the base plate thereof, is utilized to provide electrical connections to the beam chopper, stepper motors in the first and second slit providing means and in rotation imparting means of said first and second stages which each comprise a plurality of gratings, and a beam directing mirror which directs a Deuterium beam and an order sorting filter means. Said mother printed circuit board is provided input from socket means that interface to the outside of the substantially enclosed space defining enclosing means via sealing means. (Note, that the only wiring per se. remaining inside said substantially enclosed space containing enclosing means is teflon™ coated and is present between the Deuterium Power Source and the Deuterium Lamp);
  electrical connections to said beam chopping means, first slit providing means, first stage comprising a plurality of gratings and associated rotation imparting means, second slit providing means, second stage comprising a plurality of gratings and associated rotation imparting means as well as the order sorting filter means are via plug-socket means on said mother printed circuit board;
  a Deuterium lamp is mounted on a stage inside said enclosing means and allows external X-Y-Z three dimensional position adjustment.

The reason for the external X-Y-Z three dimensional position adjustment stage is that it has been found when a Deuterium Lamp is replaced, the new one is typically slightly different than the old one and the beam it provides does not exactly follow the prior Lamp locus. Mounting it on the described stage and adjusting its X-Y-Z position however, enables the new Lamp to be oriented so that the beam is directed substantially as was the beam from the replaced Deuterium lamp. (Note, the beam from the Deuterium lamp is guided by a stepper motor driven source selecting mirror, which does not require adjustment when a Deuterium Lamp is changed if the stage is properly adjusted). However, it must be appreciated that the X-Y-Z adjustment is preferably conducted while a new Deuterium lamp is operating in an atmosphere purged of oxygen and water vapor, so that ultraviolet wavelengths are not absorbed thereby. Adjustment controls for the X and Y and Z stage positioning must then be accessible from the outside of the substantially enclosed space containing enclosing means, and said adjustment controls are, in the present J.A. Woollam Co. monochromator embodiment, located near one another and adjacent to the Deuterium Lamp supporting stage, with access to said controls being from outside said substantially enclosed space enclosing means. Prior to implementation of said exteriorly controlled X-Y-Z stage adjustment of the Deuterium Lamp position, adjustment of its positioning was very difficult and required opening the substantially enclosed space.

An additional point of novelty comprises not only the mounting of the Deuterium Lamp on an X-Y-Z exteriorly adjusted stage, but also a novel approach to effecting said X-Y-Z adjustments of the stage. As mentioned, all adjustments are accessible outside the enclosing means very near to the location of the stage which enables the X-Y-Z three dimensional position adjustment just inside the enclosing means. This, of course requires some sort of force re-directing means for two, (ie. longitudinal and vertical), of the degrees of freedom. While force can be easily applied to the stage which allows the X-Y-Z three dimensional position adjustment to move the Deuterium Lamp laterally in the enclosing means, (eg. the "X" direction), means to direct similarly directed applied force to effect longitudinal (Y) and vertical (Z) motion is required. The novel approach taken to said direction of force translation is to provide curved grooves in material, into which grooves are loosely secured a number of balls. Applying lateral force to the first such ball in sequence thereof, causes longitudinal or vertical motion of the last ball in two sequences thereof respectively. Spring biasing of the stage against positive applied lateral, longitudinal or vertical motion, provides for the ability of the stage to be both pushed and retracted in any of the three X-Y-Z lateral, longitudinal and vertical directions.

In summary, improvements to the monochromator system disclosed in the Background Section include the presence of a wire eliminating "Mother Printed Circuit Board" inside a substantially enclosed space of an enclosing means which electrically interconnects to slit control, grating control and source mirror selection control stepper motors and order sorting filter means via plug-socket means. Further, stepper motor driving electronic components are mounted to a Second Printed-Circuit Board which is mounted outside said enclosing means and which plugs to the Mother Board at a projection thereof, through sealing means in a wall of the enclosing means. This makes replacement of faulty electronics easy to accomplish in the case of trouble, without requiring opening the substantially enclosed space to atmosphere. In particular, the absence of nearly all wiring from inside the substantially enclosed space has been shown to reduce degradation, over time, of electromagnetic radiation beam intensity throughput which can result from wire coating polymer depositions onto mirror and grating surfaces. The minimal wiring remaining inside said substantially enclosed space, (eg. to provide power to a Deuterium Lamp), is teflon™ coated. This elimination of most wiring inside the substantially enclosed space is especially valuable as utilization of wavelengths below 157 nm is expanded in semiconductor work, as it is said shorter wavelengths which are most effected by said polymer depositions. A further improvement is that a Deuterium Lamp source present in said substantially enclosed space is mounted on a stage which provides externally controlled X-Y-Z position adjustment capability, again without the requirement that the substantially enclosed space be opened to the atmosphere.

A primary Application of the disclosed Monochromator System is in a Spectrophotometer, Polarimeter or Ellipsometer System which comprises a Polarization State Generator System, a Sample System Supporting Stage, and a Polarization State Detection System. Further, as said Monochromator finds application in Visible and VUV wavelength ranges, a preferred Polarization State Detection System comprises multiple detectors which can be sequentially placed into a beam of electromagnetic radiation after it interacts with a Sample System placed on the Sample System Supporting Stage.

An ellipsometer system for instance, can, in functional combination with said monochromator, comprise:
  a source system comprising:
    a source of electromagnetic radiation: and a polarization state modifier system:
    a stage for supporting a sample system;
  a plurality of polarization state detector systems, each of which comprises:
    a polarization state analyzer: and
    a detector system;

such that a beam of electromagnetic radiation is produced by said source of electromagnetic radiation and caused to pass through said polarization state modifier system, interact with a sample system placed on said stage for supporting a sample system, pass through a polarization state analyzer and enter a detector system in the pathway thereof. The mounting of said plurality of polarization state detector systems is typically in a manner which allows easily, sequentially, via mechanical motion, placing a first and then a second thereof so as to receive said beam of electromagnetic radiation, without required removal of any of said plurality of polarization state detector systems from said ellipsometer system.

A spectrophotometer system, can, in functional combination with said monochromator, comprise:
  a source of electromagnetic radiation;
  a stage for supporting a sample system; and
  a plurality of detector systems;

such that a beam of electromagnetic radiation is produced by said source of electromagnetic radiation and caused to interact with a sample system placed on said stage for supporting a sample system, and enter a detector system in the pathway thereof. The plurality of detector systems is preferably mounted in a manner which allows easily, sequentially placing a first and then a second thereof so as to receive said beam of electromagnetic radiation without required removal of any of said plurality of detector systems from said spectrophotometer system.

Stated alternatively, the disclosed invention can comprise, in functional combination with the monochromator, a system selected from the group consisting of:
  spectrophotometer;
  ellipsometer; and
  polarimeter;

said system comprising:
  a polarization state detector system comprising:
    a polarization state analyzer: and
    a multiple detector system;

such that a beam of electromagnetic radiation is caused to pass through said polarization state analyzer in the pathway thereof, then enter a detector system;

wherein the improvement comprises the presence of at least a first, and a second, detector system, said first and second detector systems being mounted in a manner which allows easily, sequentially, via mechanical motion, placing one and then the other thereof so as to receive said beam of electromagnetic radiation without the requirement that any detector system be removed from said spectrophotometer, ellipsometer or polarimeter system.

Another recitation provides that, in combination with the monochromator, the disclosed invention is a system selected from the group consisting of:
- spectrophotometer;
- ellipsometer; and
- polarimeter;

said system comprising:
- a polarization state detector system comprising:
  - a polarization state analyzer which contains means for selecting at least one electromagnetic beam polarization state(s): and
  - a detector system;

such that a beam of electromagnetic radiation is caused to follow a path selected from the group consisting of:
- pass through a means for selecting at least one electromagnetic beam polarization state(s) in said polarization state analyzer;
- not pass through a means for selecting at least one electromagnetic beam polarization state(s) in said polarization state analyzer;

before entering said detector system;

wherein the improvement is a means for easily, sequentially, via mechanical motion, positioning said means for selecting at least one electromagnetic beam polarization state(s) in said polarization state analyzer.

In any of the above described systems which include the monochromator as part thereof, said plurality of detector systems includes at least two different types of detector systems, at least one thereof being selected from the group consisting of:
- photo-diode;
- photo-diode array;
- charge-coupled-device;
- photo-multiplier tubes;
- photo-resistive elements;
- photo-conductive elements;
- thermo-piles;
- bolemeters; and
- having detector system distinguishing aperturing present.

It is noted that the source of electromagnetic radiation in a spectrophotometer, polarimeter or ellipsometer system can properly be considered a part of the monochromator.

The disclosed invention will be better understood by reference to the Detailed Description Section of this Specification, in combination with the Drawings.

SUMMARY OF THE INVENTION

It is therefore a purpose and/or objective of the disclosed invention to teach an improved monochromator.

It is another a purpose and/or objective of the disclosed invention to teach application of a monochromator in polarimeter, ellipsometer and spectrophotometer systems which comprise a plurality of polarization state detector systems which are mounted in a manner which allows easily, sequentially, via mechanical motion, placing a first and then a second thereof so as to receive said beam of electromagnetic radiation, without required removal of any of said plurality of polarization state detector systems from said ellipsometer or polarimeter system.

Other purposes and/or objectives of the disclosed invention will be appreciated by a reading of the Specification and claims.

DETAILED DESCRIPTION

Figure 1A:
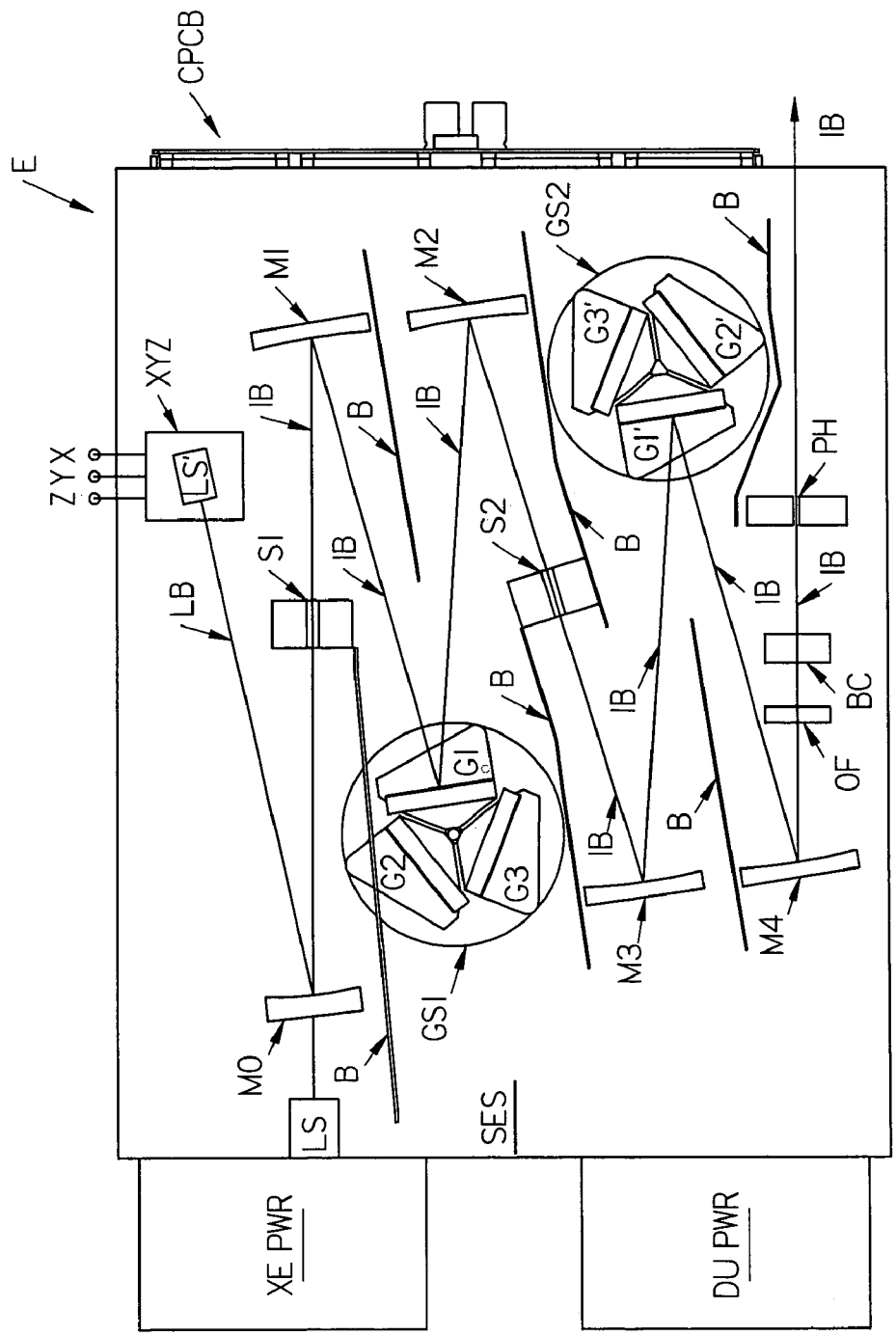
FIG. 1a shows an enclosing means (E) which contains an substantially enclosed space (SES) in which are shown components of a disclosed monochromator system.
Figure 2:
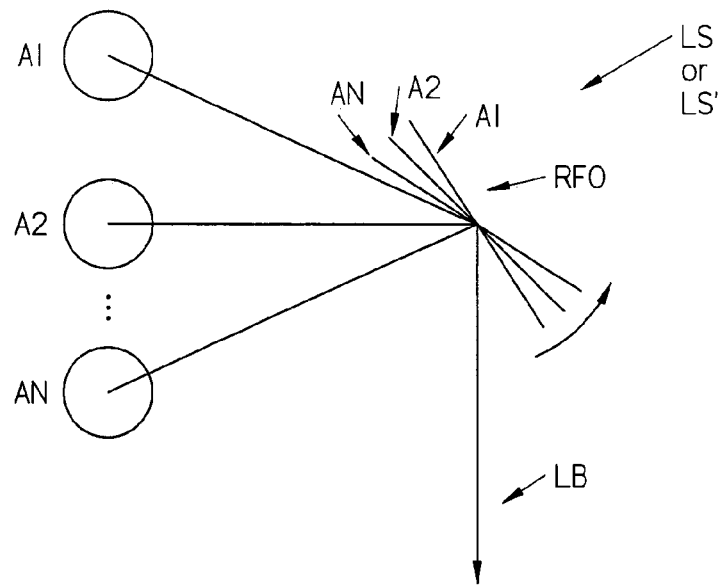
FIG. 2 shows a multiple lamp source of electromagentic radiation.

FIG. 1a shows the functional layout of a disclosed monochromator. Shown in an enclosing means (E) are sources of polychromatic electromagnetic radiation (LS) (LS'), a source selecting mirror (M0), a first slit (S1), a first mirror (M1), a first grating system (GS1) comprising three gratings (G1) (G2) AND (G3) on a rotation imparting stage (GS1), a second mirror (M2), a second slit (S2), a third mirror (M3), a second grating system (GS2) comprising three gratings (G1') (G2') AND (G3') on another rotation imparting stage (GS2), a fourth mirror (M4), an order sorting filter means (OF), a beam chopper means (BC), and a pinhole (PH). The source selecting mirror is shown positioned to direct electromagnetic radiation from source (LS') toward the first slit (S1). Note also the presence of baffling (B) to block stray electromagnetic radiation from interfering with the intended beam (IB). The power supplies for Xenon (XePWR) and Deuterium (DuPWR) lamps are also indicated. FIG. 2 is included to show that (LS) and/or (LS') can comprise multiple Lamps (A1) (A2) ... (AN) and an orientable means (RFO), (eg. shown as reflective), for selection therebetween, when, for instance, a lamp burns out.

Figure 1B:
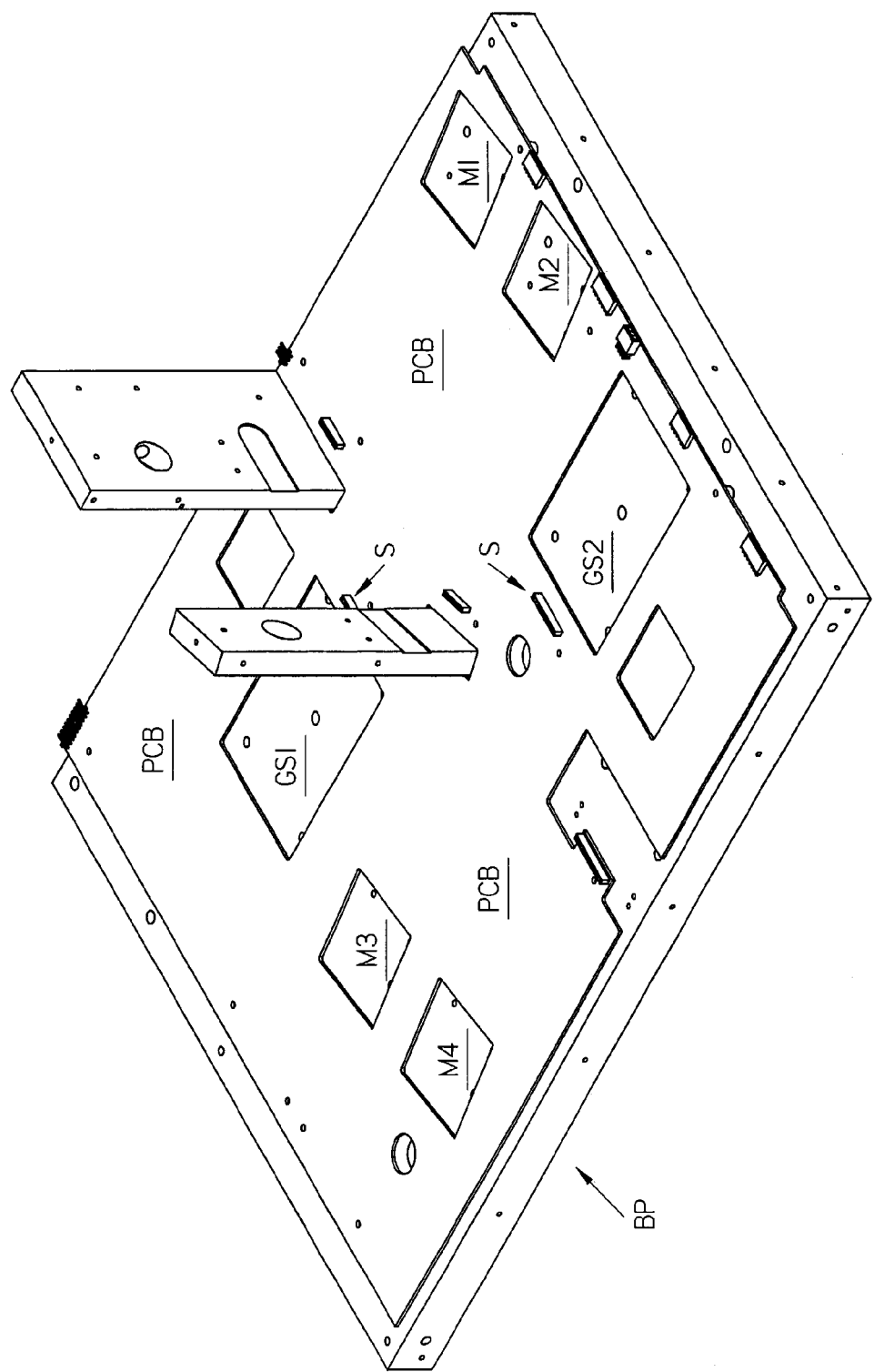
FIG. 1b shows a perspective view of the Mother PC Board of a disclosed invention improved monochromator.

FIG. 1b shows a perspective view of a baseplate (BP) of the monochromator with a mother printed circuit board (PCB) positioned thereabove. Note that FIG. 1b shows openings are present in the mother printed circuit board (PCB) to allow access to the baseplate (BP) for mounting thereto the above identified (M1), (M2), (M3), (M4), (GS1), (GS2), (BC), (OF), (PH), (S1), (S2) and also note the presence of sockets (S) for inserting plugs-in means near (GS1) and (GS2). In use electrical connections to rotation imparting stepper motors in (GS1) and (GS2) are easily made to said sockets (S). While not shown, the disclosed invention provides for electrical connections via such sockets for stepper motors in slit providing means and beam chopping means as well. The presence of the printed circuit board and the use of sockets to facilitate electrical connections therefor to stepper motors is an improvement over previously known embodiments of the J.A. Woollam CO. monochromator.

Figure 1C:
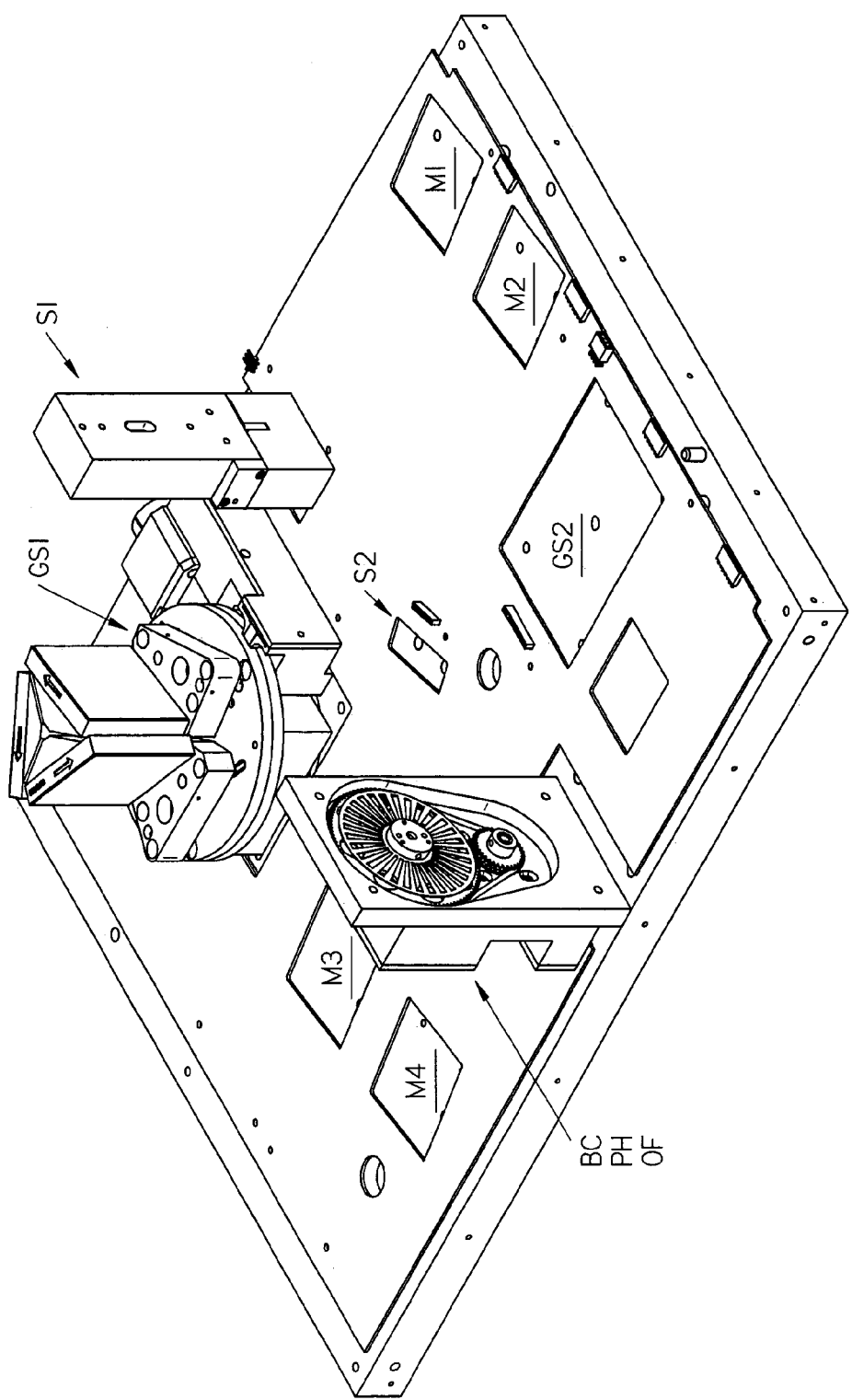
FIG. 1c shows a perspective view of the Mother PC Board of a disclosed invention improved monochromator showing the First (S1) Slit.

FIG. 1c shows a perspective view of the Mother PC Board of a disclosed invention improved monochromator showing the First (S1) plug-in Slit, rotation imparting stage (GS1), and a combination Beam Chopper (BC)-Pin Hole (PH) providing means-Order Selecting Filter (OF) positioned in place via a socket.

Figure 1D:
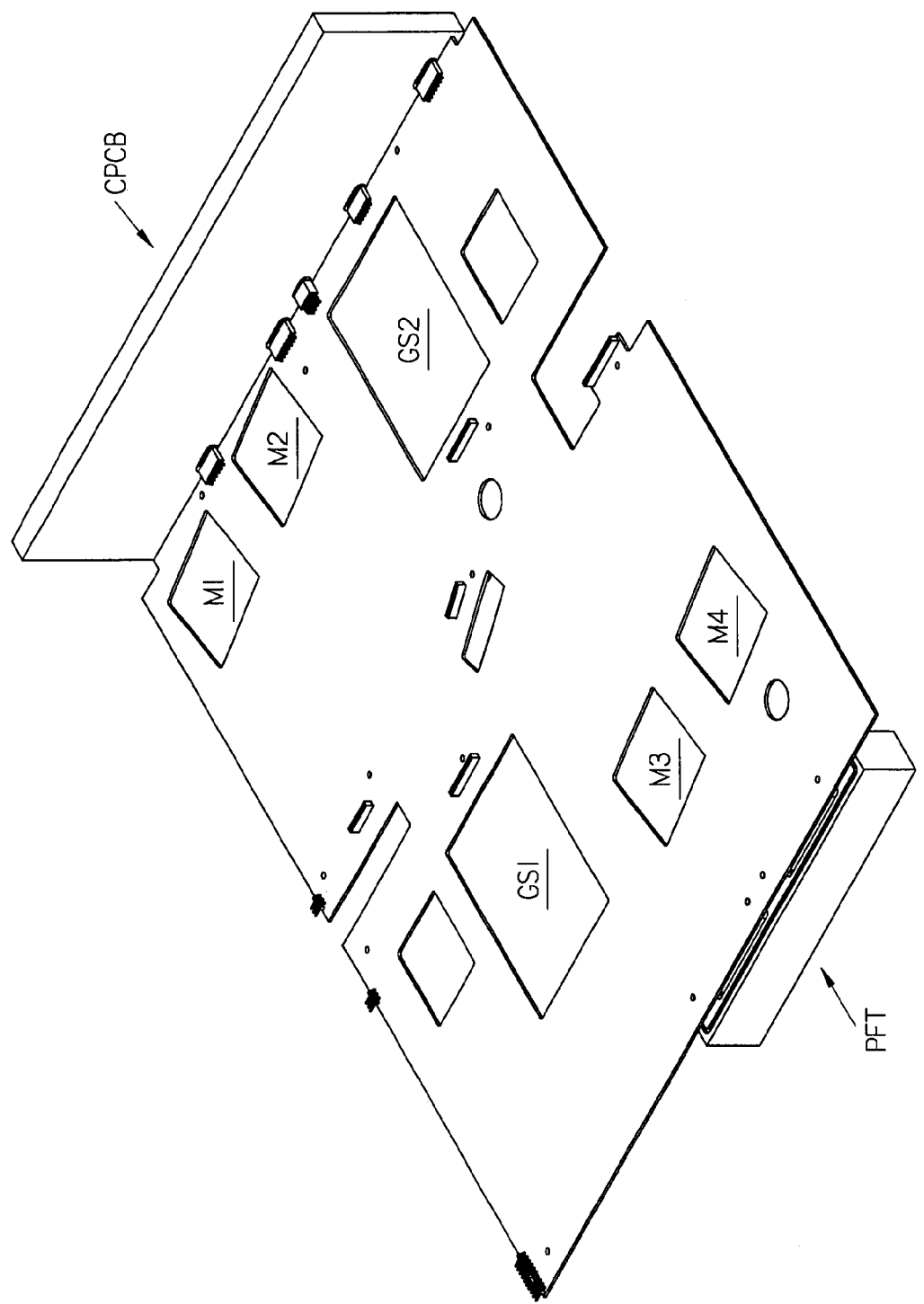
FIG. 1d shows a perspective view of the Mother PC Board of a disclosed invention improved monochromator showing Power Feedthrough (PFT) and Component Printed Circuit Board (CPCB).

FIG. 1d shows a perspective view of the Mother PC Board of a disclosed invention improved monochromator showing Power Feedthrough (PFT) and the location of a Component Printed Circuit Board (CPCB) which is present externally to the substantially enclosed space enclosing means (E) shown in FIG. 1a, and which has stepper motor driving circuitry present thereupon. Note FIG. 1a shows the Component Printed Circuit Board (CPCB) which helps to coordinate the system as viewed in differently in FIGS. 1a and 1d.

Figure 3A:
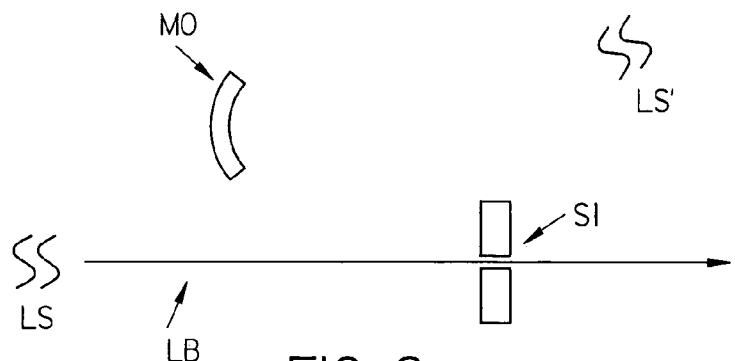
FIG. 3a shows a Xenon source (LS) configuration in the monochromator.
Figure 3B:
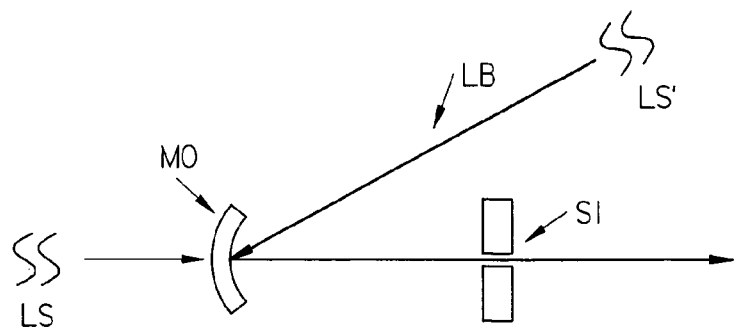
FIG. 3b shows a Deuterium source (LS) configuration in the monochromator.

FIG. 3a shows the source of polychromatic electromagnetic radiation (LS), a second source of polychromatic electromagnetic radiation (LS'), and a source selecting mirror (M0) oriented to allow electromagnetic radiation from the source (LS) to enter said first slit (S1). FIG. 3b shows the source selecting mirror (M0) can be entered to allow polychromatic electromagnetic radiation to be provided by (LS') to be directed toward said first slit (S1). This can be of benefit where, for instance, (LS) is a Xenon lamp; and (LS') is a Deuterium lamp, to enable providing wavelengths between 135 nm to 190 nm, and from 190 nm up to 2000 nm, respectively.

Figure 4A:
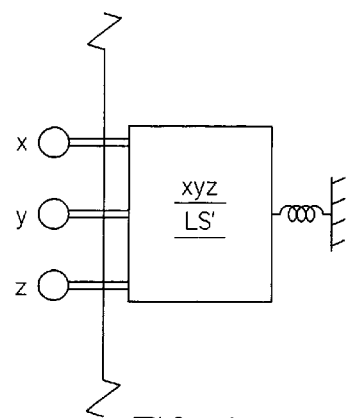
FIG. 4a is functionally a top view of a position adjustable stage (XYZ), which allows "X", "Y" and "Z" direction adjustment.
Figure 4B:
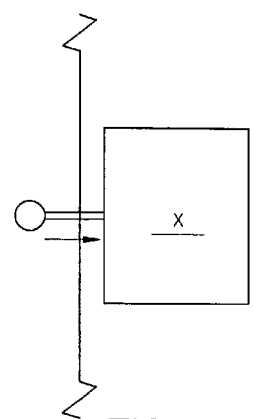
FIG. 4b is functionally a top view of a lateral "X" direction control means which accesses said XYZ position adjustable stage.
Figure 4C:
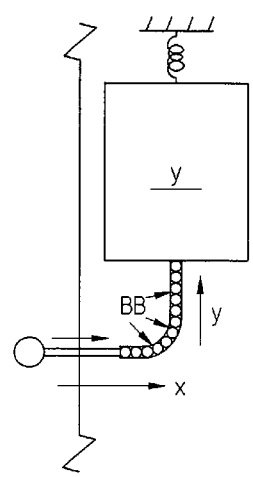
FIG. 4c is functionally a top view of a longitudinal "Y" direction control means which enables applying force laterally in the "X" direction, and via a sequence of balls present in a groove, applies "Y" direction force longitudinally.
Figure 4D:
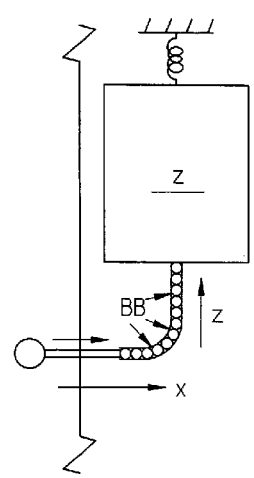
FIG. 4d is functionally a side elevational view of a vertical "Z" direction control means which enables applying force vertically in the "X" direction, and via a sequence of balls present in a groove, applies "Z" direction force longitudinally.
Figure 4E:
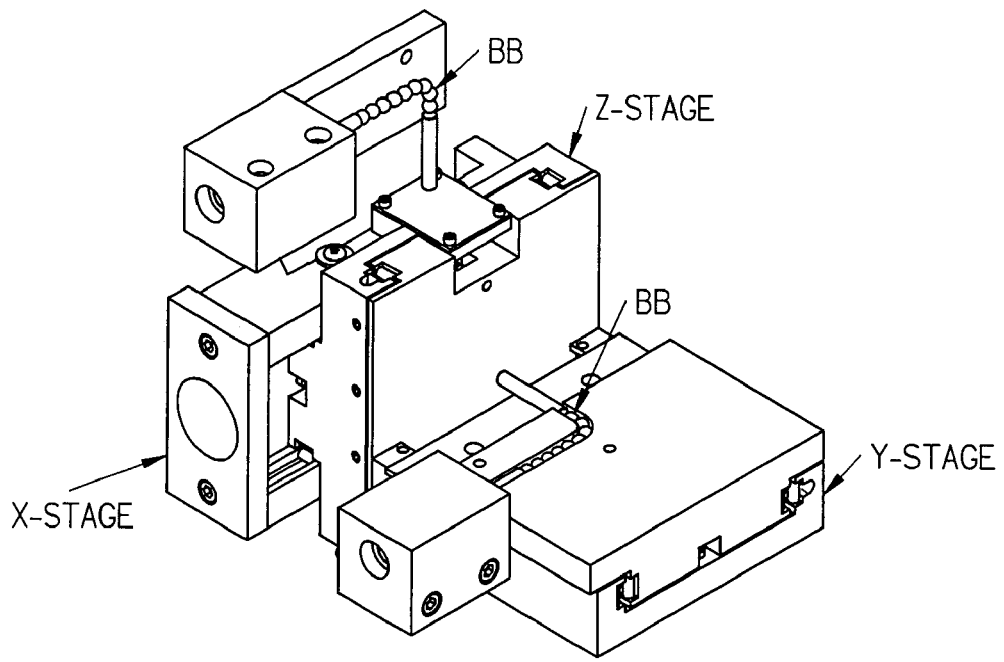
FIGS. 4e and 4f show perspective views of the position adjustable stage (XYZ) of FIGS. 4a–4d.
Figure 4F:
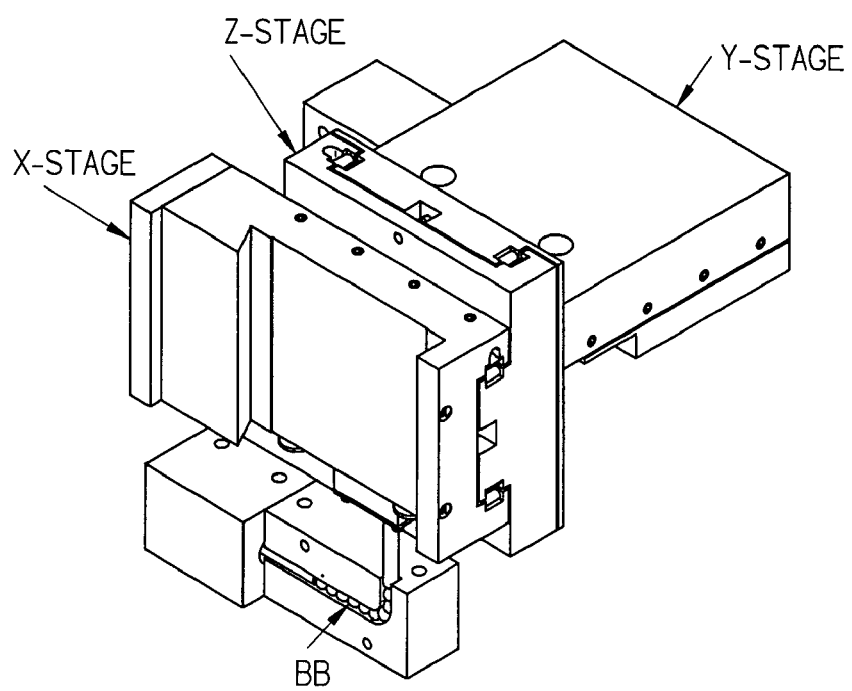

FIG. 4a is functionally a top view of a position adjustable stage (XYZ) indicated in FIG. 1a, which allows "X", "Y" and "Z" direction adjustment from outside the FIG. 1a indicated enclosing means (E). FIG. 4b is functionally a top view of a lateral "X" direction control means shown in FIG. 1a, which accesses said XYZ position adjustable stage (XYZ) and applies lateral force directly thereto. FIG. 4c is functionally a top view of a longitudinal "Y" direction control means shown in FIG. 1a, which enables applying force laterally in the "X" direction, and via a sequence of balls present in a groove, applies "Y" direction force longitudinally to stage (XYZ). FIG. 4d is functionally a side elevational view of a vertical "Z" direction control means shown in FIG. 1a, which enables applying force laterally in the "X" direction, and via a sequence of balls (BB) present in a groove, applies "Z" direction force vertically to stage (XYZ). FIGS. 4e and 4f show two perspective views of the XYZ Stage identified in FIGS. 4a–4d, and positioned as shown in FIG. 1a.

Figure 5A:
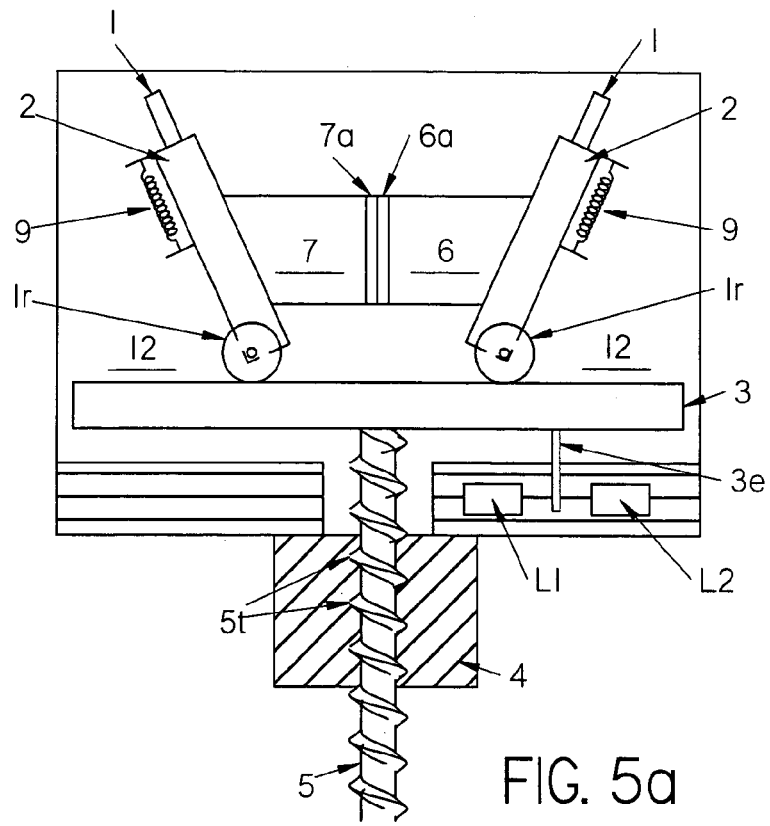
FIG. 5a shows a bi-lateral slit effecting mechanism in the monochromator.

FIG. 5a shows detail of an embodiment of a slit providing system. Elongated rail elements (1) are affixed to frame (12) and slide elements (2) are associated with each elongated rail element (1). Knife-blades (6) and (7) with facing edges (6a) and (7a) are affixed to said slide elements (2) as are rollers (1r). Rollers (1r) rest upon stage (3) and are held in contact therewith by elongated springs (9). Threaded shaft (5) is present in computer driven stepper motor (4) and serves to provide vertically oriented linear motion to said stage (3) in use via thread (5t) translated rotational shaft (5) motion. Also shown are extension element (3e), light beam transmitter (L1) and light beam detector (L2). The first (S1) and second slit (S2) providing means then each comprise a slit which is effected by a bilateral slit assembly which comprises two slide assemblies, each slide assembly comprising an elongated rail element (1) and a slide element (2) such that said slide element (2) can slide with respect to said elongated rail element (1) in the direction of elongation thereof, wherein said two slide assemblies are oriented, by affixing said elongated rail elements to a frame (12), such that slide element's loci of motion converge toward a lower extent of said frame, as said bilateral slit assembly is viewed in vertically oriented frontal elevation, thereby forming an upward opening "V" shape therebetween, the lower ends of each slide element (2) comprising means for allowing horizontal motion therebetween when said slide element (2) lower ends are caused to simultaneously move vertically during use, which bilateral slit assembly further comprises two knife-blade elements (6) (7), one affixed to each slide element (2) such that a horizontal slit width between vertically oriented facing edges (6a) (6b) of said two knife-blade elements can be controlled between essentially zero (0) distance and some larger distance by a simultaneous vertically oriented motion of the lower ends of said slide elements (2) during use. The purpose of controlling said horizontal slit width between vertically oriented facing edges (6a) (7a) of said two knife-blade elements (6) (7) being to control the intensity and frequency bandwidth of a light beam which can pass therebetween, as is required by spectrometers, monochromators, and spectrographs and the like. Said means for causing the simultaneous motion of said slide elements during use is a precisely controlled computer driven stepper motor (4) which causes a threaded motor shaft (5) therein to move vertically as a result of screw thread (5t) translation of motor (4) imparted rotational motion to said threaded motor shaft (5), said vertical motion causing said slide elements (2) to simultaneously move vertically during use, said precisely controlled computer driven stepper motor (4) being firmly affixed to said frame (12) so that the relative positioning between it and the slide assemblies is rigidly fixed during use.

Figure 5B:
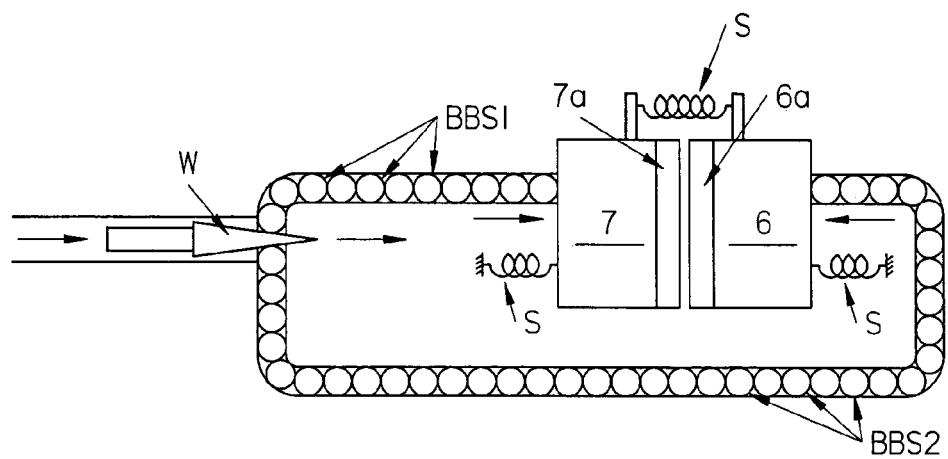
FIG. 5b shows an alternative bi-lateral slit effecting mechanism in the monochromator.

FIG. 5b shows an alternative and new design for first (S1) and second (S2) slit providing means comprises two knife-blade elements (6) (7), mounted such that a horizontal slit width between vertically oriented facing edges (6a) (7a) of said two knife-blade elements (6) (7) can be controlled between essentially zero (0) distance and some larger distance by horizontal oriented motion of one or the other thereof during use. Motion translation is preferably via motion of a wedge (W) which contacts two sequences of balls (BBS1) (BBS2), the first in each sequence of balls contacting the wedge and the last ball in one sequence (BBS1) contacting one of the two knife blades (7), and the last ball in the other sequence (BBS2) contacting the other of the two knife blades (6). Causing the wedge (W) to move causes the first ball in each sequence of balls to move and in turn the last ball in each sequence effects motion of the knife blade (6) (7) it contacts.

Figure 6:
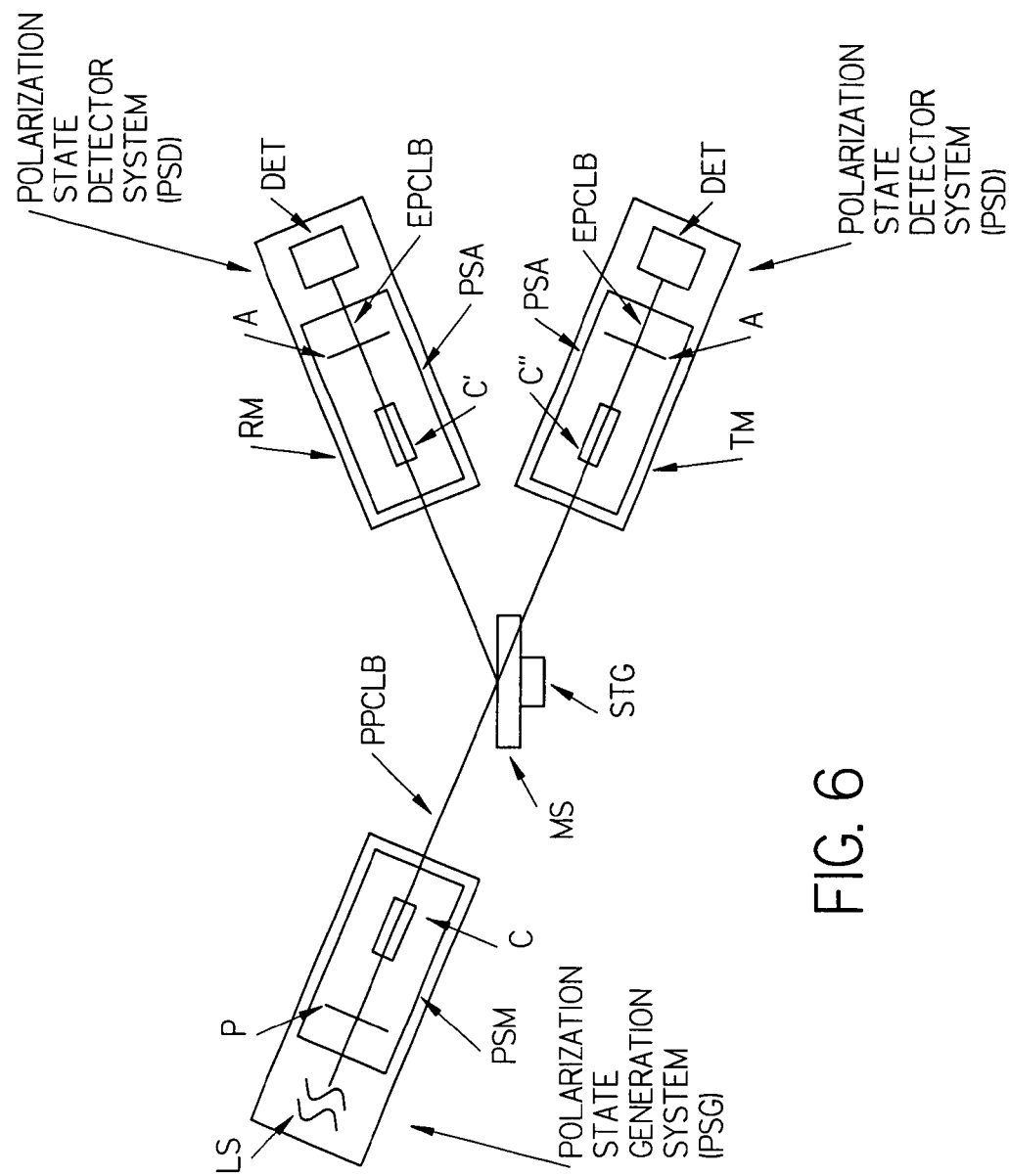
FIG. 6 shows a diagram of an ellipsometer system with both reflection and transmission detectors.

Turning to FIG. 6, there is shown a diagram of an ellipsometer/polarimeter system for use in both reflection (RF) and transmission (TM) modes. A source of monochromatic or polychromatic electromagnetic radiation (LS) is shown to, via polarization state modifier (PSM), which is demonstrated as being comprised of an Polarizer (P) and optionally a Compensator (C), provide a polarized beam of electromagnetic radiation (PPCLB) which is directed to interact with a sample system (MS) which is placed on a stage (STG) as beam (EPCLB). (Note that conventional terminology identifies a SOURCE SYSTEM as a combination of said source of monochromatic or polychromatic electromagnetic radiation (LS) and a Polarization State Modifier (PSM), which Polarization State Modifier (PSM) is demonstrated as being comprised of a Polarizer (P) and optionally a Compensator (C)). After interaction with the sample system (MS), propagated electromagnetic beam (PPCLB) emerges as (EPCLB), passes through a polarization state analyzer (PSA) and enters a detector system (DET). (Note that conventional terminology provides that for each of the Reflection (RM) and Transmission (TM) Modes, a Polarization State Analyzer (PSA) is demonstrated as being comprised of an Analyzer (A) and optionally a Compensator (C') or (C") respectively, and that when said Polarization State Analyzer (PSA) is combined with a Detector System (DET), there is formed a Reflection or Transmission Mode Polarization State Detector System, respectively). It is also to be understood that if the Polarization State Modifier (PSM), and Polarization State Analyzer (PSA) are not present, then FIG. 6 demonstrates a Spectrophotometer system comprised of (LS), (STG/(MS) and (DET). It is to be understood that the angle of incidence of the electromagnetic beam (PPCLB) is often oriented closer to normal to the sample system (MS) upper surface, when the system is operated as a Spectrophotometer. With regard to the present invention, it is to be appreciated that the Detector System(s) (DET) indicated are multiple detector systems mounted on a positionable means (eg. a movable arm), thereby allowing easy alternate positioning of the Detector Systems in at least two locations. Note that such a rotation would be in a vertically oriented plane, as shown in FIG. 6, but that this is only demonstrative and in any embodiment of the present invention multiple detector system, motion in any plane is within the scope of the claims, (eg. see FIGS. 7a and 7b). Note further that any functional means for modifying or analyzing a polarization state is to be considered within the scope of the exemplary polarizer/compensator, compensator/analyzer combinations demonstrated in FIG. 6.

Figure 7A:
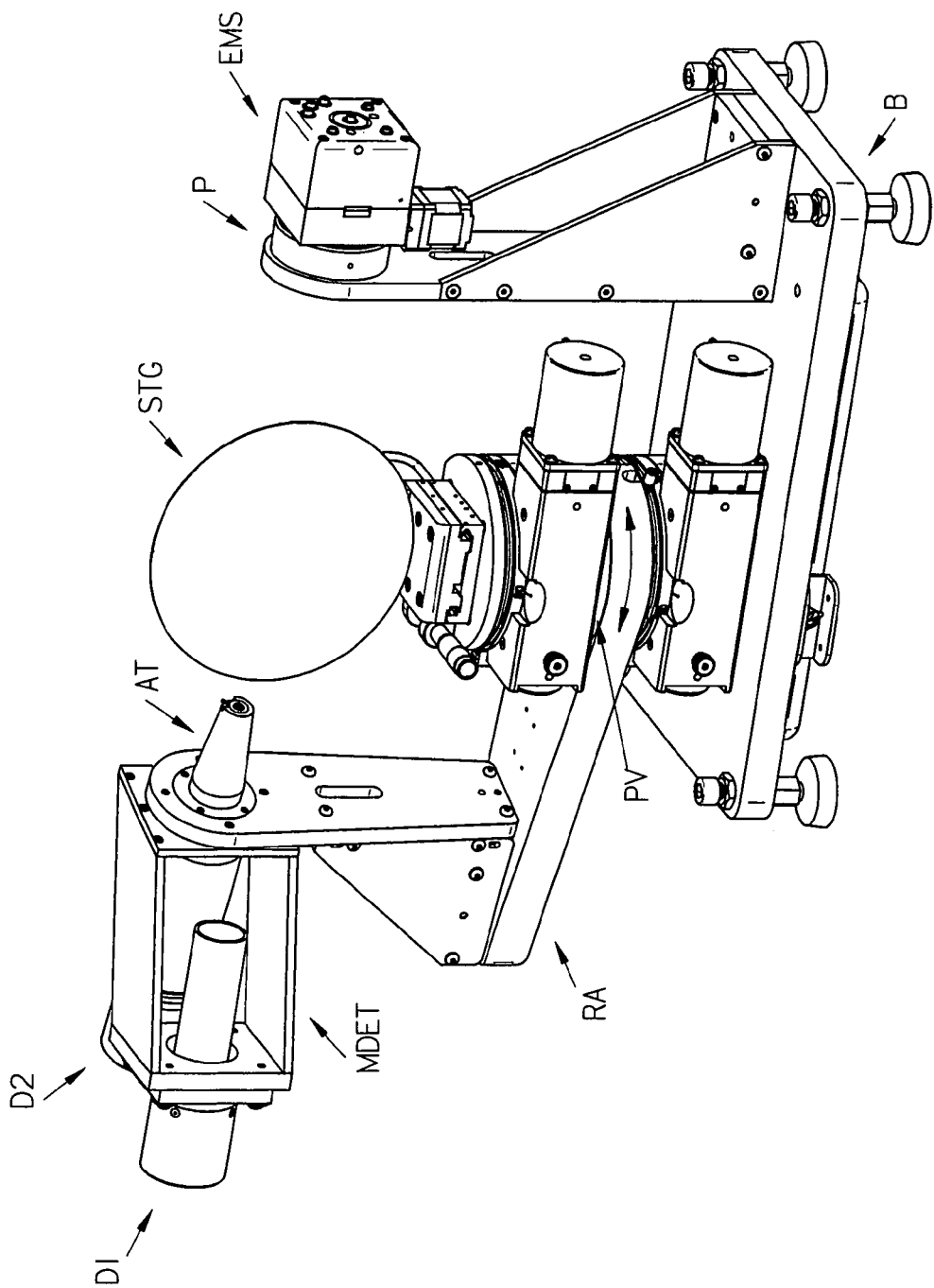
FIG. 7a shows an ellipsometer system configured to apply an electromagnetic beam to a sample system in a reflection mode.

Turning now to FIG. 7a, there is shown a preferred embodiment of a Detector System for application in disclosed invention polarimeter, ellipsometer and spectrophotometer systems which operate over a large wavelength range. Shown mounted to a common base (B), are a source of electromagnetic radiation (EMS) and a polarizer (P), a stage (STG) for supporting a sample system in use, and a multiple detector system (MDET) which is comprised of two detector systems, (eg. first (D1) and second (D2) detector systems). One of the first (D1) and second (D2) detector systems might be appropriate for detecting ellipsometric signals, and one for detecting spectrophotometric signals, or Detectors (D1) and (D2) might be sensitive in different wavelength ranges. Aperture (AT) can be included to limit entry of electromagentic radiation.

Note that both first (D1) and second (D2) detector systems are mounted to rotatable arm (RA), and that rotatable arm (RA) is rotatable about a pivot point (PV). In use it is easy for a user to, directly or via an automation system, rotate either the first (D1) or second (D2) detector system into place, while performing, for instance, calibration or data acquisition, respectively. Note that the such a rotation is shown in a horizontally oriented plane, but could be oriented in a vertically oriented plane as suggested by FIG. 6. Rotation in any plane is within the scope of the present invention.

Figure 7B:
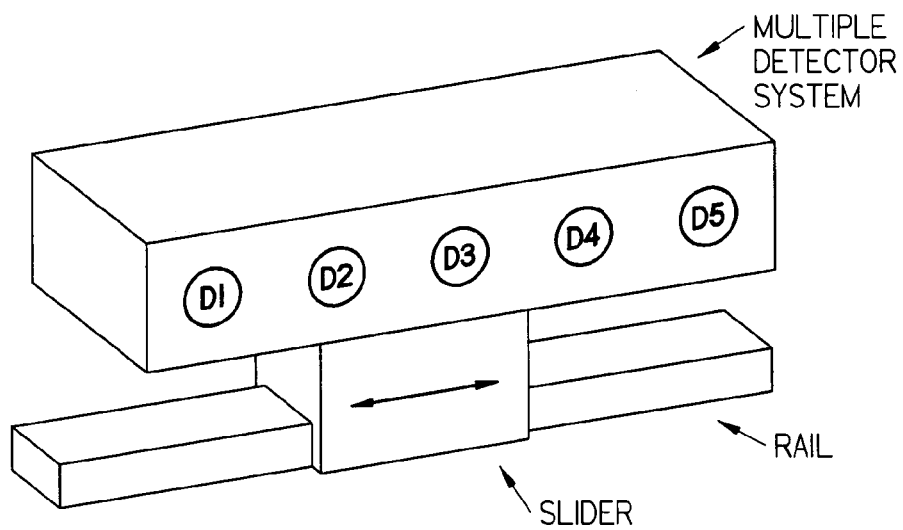
FIGS. 7b and 7c show, as does FIG. 1a, multiple detectors affixed to a system such that any thereof can be mechanically positioned to receive an electromagnetic beam.
Figure 7C:
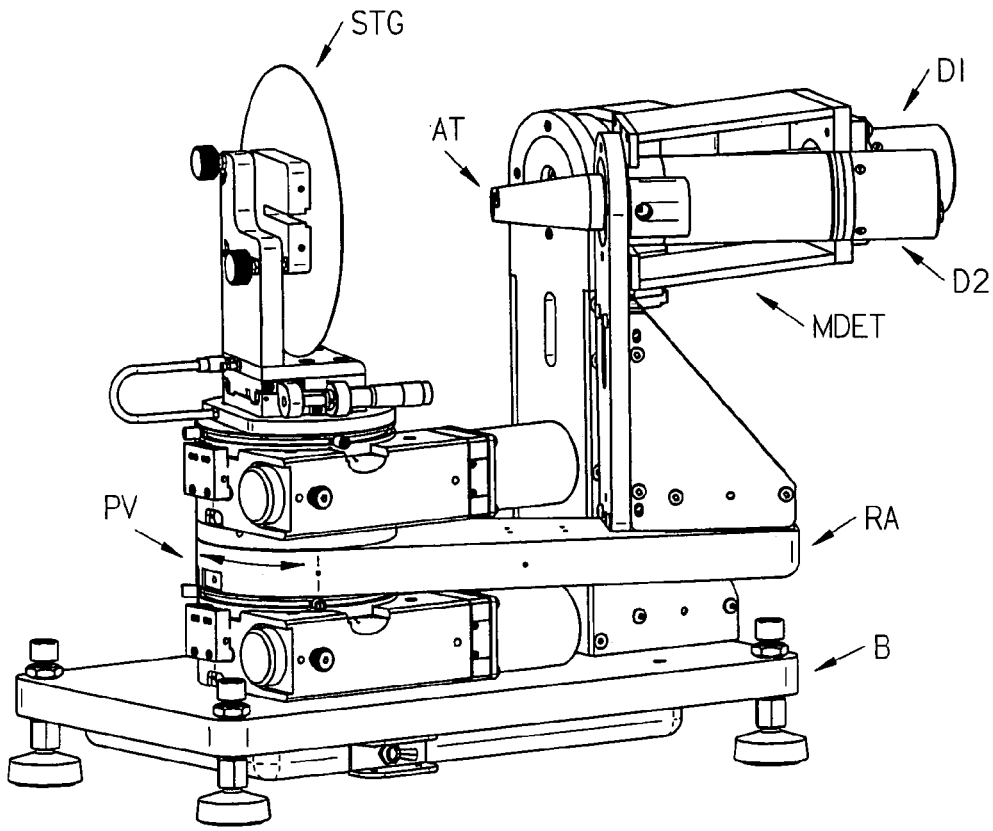

FIG. 7c shows a partial, alternative view, of the preferred embodiment of the present invention shown in FIG. 7a. Functional equivalents to the geometry shown in FIGS. 7a and 7c are within the scope of the present invention.

FIG. 7b demonstrates an alternative means, (linear rail and slider), for providing a plurality of positionable detector systems. Of course in a present invention system, said FIG. 7b can be oriented so that the Multiple Detector System slides horizontally or vertically or in between, with respect to an external frame of reference.

It is to be understood that the various "mirrors" identified can be of anyfunctional type, (eg. torroidal, off-axis-parabolic, spherical etc.), but that to date the preferred embodiment has utilized spherical mirrors.

It is also specifically noted that while the "Beam Chopper" is typically positioned just before the "Pin Hole" in the "Pin Hole Providing Means", it can be positioned at any functional location between the Source of the Electromagnetic radiation and the pin hole, or even beyond the pin hole (PH) providing means and/or outside the enclosed space enclosing means (E).

Finally, it is noted that during calibration the FIG. 1a Sources (LS) and (LS') can be functionally replaced by a third, known wavelength Source, such as a Pen Light, which is temporarily inserted into the monochromator system. For this purpose, a "Port Providing Means", (not shown), can be present and conventiently located at any functional location, to allow insertion of said third source.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A monochromator system for selecting a small range of wavelengths in a polychromatic beam of electromagnetic radiation, which monochromator system functionally sequentially comprises within in a substantially enclosed space containing enclosing means having vertical, longitudinal and lateral dimensions:
    source means for providing of a beam of electromagnetic radiation;
    first slit providing means;
    first mirror;
    first stage comprising a plurality of gratings, each of which can be rotated into a functional position;
    second mirror providing element;
    second slit providing means;
    third mirror;

second stage comprising a plurality of gratings, each of which can be rotated into a functional position;

fourth mirror;

order sorting filter means;

pin hole providing means;

and further comprises beam chopper means after said source means for providing of a beam of electromagnetic radiation;

said source means for providing a beam of electromagnetic radiation comprising both Xenon and Deuterium Lamps and source selecting mirror and motion imparting means for selecting therebetween;

said second mirror being laterally present between said first mirror and said second stage which comprises a plurality of gratings, and said third mirror being laterally positioned between said first stage which comprises a plurality of gratings and said fourth mirror, said first mirror and second mirror and said second stage comprising a plurality of gratings as a group being longitudinally removed from said first stage which comprises a plurality of gratings and said third mirror and said fourth mirror;

there being first electromagnetic radiation blocking baffle means positioned between said source means for providing of a beam of electromagnetic radiation and said first stage comprising a plurality of gratings;

there being second electromagnetic radiation blocking baffle means positioned between said second mirror providing element and said second stage comprising a plurality of gratings;

there being third electromagnetic radiation blocking baffle means positioned between said third mirror providing element and said first stage comprising a plurality of gratings;

there being fourth electromagnetic radiation blocking baffle means positioned between said first and second mirrors;

there being fifth electromagnetic radiation blocking baffle means positioned between said third and fourth mirrors;

there being sixth electromagnetic radiation blocking baffle means positioned between said second stage comprising a plurality of gratings and said pin hole providing means;

such that in use a beam of electromagnetic radiation provided by said source means for providing of a beam of electromagnetic radiation is:

caused to pass through said first slit;

reflect from said first mirror;

interact with one of said plurality of gratings on said first stage which is rotated into a functional position;

reflect from said second mirror;

pass through said second slit;

reflect from said third mirror;

interact with one of said plurality of gratings on said second stage which is rotated into a functional position;

reflect from said fourth mirror, proceed through order sorting filtering means;

said beam of electromagnetic radiation further being chopped by said chopping means;

with monochromator selected wavelengths being caused to exit through said pinhole;

the improvements being that:

said Deuterium lamp is mounted on a stage which enables three dimensional X-Y-Z positioning motion controlled from outside said enclosing means;

said beam chopping means, source selecting mirror and motion imparting means, first slit providing means, first stage comprising a plurality of gratings and associated rotation imparting means, second slit providing means, second stage comprising a plurality of gratings and associated rotation imparting means, all have electrical plug-in/socket means;

and a mother printed circuit board which provides traces which in use carry electrical energy to said source selecting mirror motion imparting means, said first slit providing means, said first stage comprising a plurality of gratings and associated rotation imparting means, said second slit providing means, said second stage comprising a plurality of gratings and associated rotation imparting means; conductive traces on said mother printed circuit board providing access at a socket means which is extended outside said substantially enclosed space defining enclosing means.

2. A monochromator system as in claim 1, in which electronic circuitry for controlling said rotation imparting means which when provided an electrical signal causes rotation of said associate first or second stage is present on a printed circuit board which plugs into said socket means of said mother printed circuit board which is extended outside said substantially enclosed space defining enclosing means via a sealing means.

3. A monochromator system as in claim 1, in which the first and second slit providing means each comprise a slit which is effected by a bilateral slit assembly which comprises two slide assemblies, each slide assembly comprising an elongated rail element and a slide element such that said slide element can slide with respect to said elongated rail element in the direction of elongation thereof, wherein said two slide assemblies are oriented; by affixing said elongated rail elements to a frame, such that slide element's loci of motion converge toward a lover extent of said frame, as said bilateral slit assembly is viewed in vertically oriented frontal elevation, thereby forming an upward opening EVA shape therebetween, the lower ends of each slide element comprising means for allowing horizontal motion therebetween when said slide element lower ends are caused to simultaneously move vertically during use, which bilateral slit assembly further comprises two knife-blade elements, one affixed to each slide element such that a horizontal slit width between vertically oriented facing edges of said two knife-blade elements can be controlled between essentially zero (0) distance and some larger distance by a simultaneous vertically oriented motion of the lower ends of said slide elements during use, the purpose of controlling said horizontal slit width between vertically oriented facing edges of said two knife-blade elements being to control the intensity and frequency bandwidth of a light beam which can pass therebetween, as is required by spectrometers, monochromators, and spectrographs and the like.

4. A monochromator system as in claim 1, in which the first and second slit providing means each comprise a slit which is effected by a bilateral slit assembly which comprises two knife-blade elements, affixed to slide elements such that a horizontal slit width between vertically oriented facing edges of said two knife-blade elements can be controlled between essentially zero (0) distance and some larger distance by horizontal oriented motion of one or the other thereof during use, said motion translation being via motion of a wedge which contacts two sequences of balls, the first in each sequence of balls contacting the wedge and the last ball in one sequence contacting one of the two knife blades, and the last ball in the other sequence contacting the other of the two knife blades, such that causing the wedge to move causes the first ball in each sequence of balls to move and in turn the last ball in each sequence effects motion of the knife blade it contacts, said first ball in one said sequence contacting one side of said wedge, and said first ball in said second sequence contacting the other said of said wedge;

the purpose of controlling said horizontal slit width between vertically oriented facing edges of said two knife-blade elements being to control the intensity and frequency bandwidth of a light beam which can pass therebetween, as is required by spectrometers, monochromators, and spectrographs and the like.

5. A monochromator system for selecting a small range of wavelengths in a beam of electromagnetic radiation, which monochromator system functionally sequentially comprises within in a substantially enclosed space containing enclosing means having longitudinal and lateral dimensions:

Deuterium source means for providing of a beam of electromagnetic radiation;
first slit providing means;
first mirror;
first stage comprising a plurality of gratings, each of which can be rotated into a functional position;
second mirror providing element;
second slit providing means;
third mirror;
second stage comprising a plurality of gratings, each of which can be rotated into a functional position;
fourth mirror;
order sorting filter means;
pin hole providing means;
and further comprises beam chopper means after said source means for providing of a beam of electromagnetic radiation;
such that in use a beam of electromagnetic radiation provided by said Deuterium source means for providing of a beam of electromagnetic radiation is:
caused to pass through said first slit;
reflect from said first mirror;
interact with one of said plurality of gratings on said first stage which is rotated into a functional position;
reflect from said second mirror;
pass through said second slit;
reflect from said third mirror;
interact with one of said plurality of gratings on said second stage which is rotated into a functional position;
reflect from said fourth mirror, proceed through order sorting filtering means;
said beam of electromagnetic radiation further being chopped by said chopping means;
with monochromator selected wavelengths being caused to exit through said pinhole;
the improvements being that:
said Deuterium source means is mounted on a stage which enables three dimensional X-Y-Z positioning motion controlled from outside said enclosing means via means which project through said enclosing means, the control for each of the "X", "Y" and "Z" direction motion providing laterally directed motion which, when exerted in a positive direction respectively:
directly moves said stage laterally in a positive "X" direction;
provides lateral motion to the first of a sequential multiplicity of balls present in a channel, which channel is shaped to direct the notion of the last of said balls longitudinally in a positive "Y" direction;
provides lateral motion to the first of a sequential multiplicity of balls present in a channel, which channel is shaped to direct the motion of the last of said balls vertically in a positive "Z" direction;
said stage having spring means functionally associated therewith which resist said positive direction lateral, longitudinal and vertical motions, such that when said means which project through said enclosing means that control the "X", "Y" and "Z" direction motions are caused to provide laterally directed motion exerted in a negative direction, respectively:
causes the stage to move laterally in a negative "X" direction;
causes the stage to move laterally in a negative "Y" direction;
causes the stage to move laterally in a negative "Z" direction.

6. A method of adjusting the position of a deuterium lamp in a monochromator system to optimize monochromator system output, comprising the steps of:

a) providing a monochromator system for selecting a small range of wavelengths In a beam of electromagnetic radiation, which monochromator system functionally sequentially comprises within in a substantially enclosed space containing enclosing means having vertical, longitudinal and lateral dimensions, said monochromator system comprising:

deuterium source means for providing of a beam of electromagnetic radiation;
first slit providing means;
first mirror;
first stage comprising a plurality of gratings, each of which can be rotated into a functional position;
second mirror providing element;
second slit providing means;
third mirror;
second stage comprising a plurality of gratings, each of which can be rotated into a functional position;
fourth mirror;
order sorting filter means;
pin hole providing means;
and further comprises beam chopper means after said source means for providing of a beam of electromagnetic radiation;
such that in use a beam of electromagnetic radiation provided by said Deuterium source means for providing of a beam of electromagnetic radiation is:
caused to pass through said first slit;
reflect from said first mirror;
interact with one of said plurality of gratings on said first stage which is rotated into a functional position;
reflect from said second mirror;
pass through said second slit;
reflect from said third mirror;
interact with one of said plurality of gratings on said second stage which is rotated into a functional position;

reflect from said fourth mirror, proceed through order sorting filtering means;

said beam of electromagnetic radiation further being chopped by said chopping means;

with monochromator selected wavelengths being caused to exit through said pinhole;

the improvement being that:

said Deuterium source means is mounted on a stage which enables three dimensional X-Y-Z positioning motion controlled from outside said enclosing means via means which project through said enclosing means, the control for each of the "X", "Y" and "Z" direction motion providing laterally directed motion which, when exerted in a positive direction respectively:

directly moves said stage laterally in a positive "X" direction;

provides lateral motion to the first of a sequential multiplicity of balls present in a channel, which channel is shaped to direct the motion of the last of said balls longitudinally in a positive "Y" direction;

provides lateral motion to the first of a sequential multiplicity of balls present in a channel, which channel is shaped to direct the motion of the last of said balls vertically in a positive "Z" direction;

said stage having spring means functionally associated therewith which resist said positive direction lateral, longitudinal and vertical motions, such that when said means which project through said enclosing means that control the "X", "Y" and "Z" direction motions are caused to provide laterally directed motion exerted in a negative direction, respectively:

causes the stage to move laterally in a negative lateral "X" direction;

causes the stage to move laterally in a negative longitudinal "Y" direction;

causes the stage to move laterally in a negative vertical "Z" direction.

b) from outside said substantially enclosed space containing enclosing means operating said mirror means for selecting between said Xenon and Deuterium lamps such that the Deuterium lamp is selected and is caused to provide electromagnetic radiation to said first slit means;

c) from outside said substantially enclosed space containing enclosing means adjusting the location of said stage which enables X-Y-Z position adjustment by causing at least one selection from the group consisting of said X, Y and Z position adjustment means, while monitoring electromagnetic radiation output from said pin hole;

to the end that said electromagnetic radiation output from said pin hole is optimized.

7. An polarimeter or ellipsometer system comprising a monochromator system, said polarimeter or ellipsometer system comprising;

a source system comprising:

a source of electromagnetic radiation: and a polarization state modifier system:

a stage for supporting a sample system; and a plurality of polarization state detector systems, each of which comprises:

a polarization state analyzer: and a detector system;

such that a beam of electromagnetic radiation is produced by said source of electromagnetic radiation and caused to pass through said polarization state modifier system, interact with a sample system placed on said stage for supporting a sample system, pass through a polarization state analyzer and enter a detector system in the pathway thereof, the mounting of said plurality of polarization state detector systems being in a manner which allows easily, sequentially, placing a first and then a second thereof so as to receive said beam of electromagnetic radiation, without required removal of any of said plurality of polarization state detector systems from said ellipsometer system;

which source of electromagnetic radiation comprises a monochromator system for selecting a small range of wavelengths in a polychromatic beam of electromagnetic radiation, which monochromator system functionally sequentially comprises within in a substantially enclosed space containing enclosing means having vertical, longitudinal and lateral dimensions:

said source of electromagnetic radiation;

first slit providing means;

first mirror;

first stage comprising a plurality of gratings, each of which can be rotated into a functional position;

second mirror providing element;

second slit providing means;

third mirror;

second stage comprising a plurality of gratings, each of which can be rotated into a functional position;

fourth mirror;

order sorting filter leans;

pin hole providing means;

and further comprises beam chopper means after said source means for providing of a beam of electromagnetic radiation;

said source means for providing of a beam of electromagnetic radiation comprising both Xenon and Deuterium Lamps and source selecting mirror and motion imparting means for selecting therebetween;

said second mirror being laterally present between said first mirror and said second stage which comprises a plurality of gratings, and said third mirror being laterally positioned between said first stage which comprises a plurality of gratings and said fourth mirror, said first mirror and second mirror and said second stage comprising a plurality of gratings as a group being longitudinally removed from said first stage which comprises a plurality of gratings and said third mirror and said fourth mirror;

there being first electromagnetic radiation blocking baffle means positioned between said source means for providing of a beam of electromagnetic radiation and said first stage comprising a plurality of gratings;

there being second electromagnetic radiation blocking baffle means positioned between said second mirror providing element and said second stage comprising a plurality of gratings;

there being third electromagnetic radiation blocking baffle means positioned between said third mirror providing element and said first stage comprising a plurality of gratings;

there being fourth electromagnetic radiation blocking baffle means positioned between said first and second mirrors;

there being fifth electromagnetic radiation blocking baffle means positioned between said third and fourth mirrors;

there being sixth electromagnetic radiation blocking baffle means positioned between said second stage comprising a plurality of gratings and said pin hole providing means;

such that in use a beam of electromagnetic radiation provided by said source means for providing of a beam of electromagnetic radiation is:
  caused to pass through said first slit;
  reflect from said first mirror;
  interact with one of said plurality of gratings on said first stage which is rotated into a functional position*
  reflect from said second mirror;
  pass through said second slit;
  reflect from said third mirror;
  interact with one of said plurality of gratings on said second stage, which is rotated into a functional position;
  reflect from said fourth mirror, proceed through order sorting filtering means;

said beam of electromagnetic radiation further being chopped by said chopping means;

with monochromator selected wavelengths being caused to exit through said pinhole;

said monochromator being characterized by at least one selection from the group consisting of:
  said Deuterium lamp is mounted on a stage which enables three dimensional X-Y-Z positioning motion controlled from outside said enclosing means;
  said beam chopping means, source selecting mirror and motion imparting means, first slit providing means, first stage comprising a plurality of gratings and associated rotation imparting means, second slit providing means, second stage comprising a plurality of gratings and associated rotation imparting means, all have electrical plug-in/socket means;
  and a mother printed circuit board which provides traces which in use carry electrical energy to said source selecting mirror motion imparting means, said first slit providing means, said first stage comprising a plurality of gratings and associated rotation imparting means, said second slit providing means, said second stage comprising a plurality of gratings and associated rotation imparting means; conductive traces on said mother printed circuit board providing access at a socket means which is extended outside said substantially enclosed space defining enclosing means.

* * * * *